:::
United States Patent [19]

Kersten et al.

[11] Patent Number: 5,181,276
[45] Date of Patent: Jan. 26, 1993

[54] INFECTION RESISTANT PRODUCTS

[75] Inventors: Jean Kersten, Villers St. Amand; Yves A. Delmotte, Tertre, both of Belgium

[73] Assignee: Baxter International Inc., Deerfield, Ill.

[21] Appl. No.: 759,695

[22] Filed: Sep. 9, 1991

Related U.S. Application Data

[63] Continuation of Ser. No. 484,137, Feb. 22, 1990, abandoned.

[51] Int. Cl.$^5$ .............................................. A41D 19/00
[52] U.S. Cl. ...................... 2/161 R; 2/167; 2/168; 252/52 A; 252/106; 252/132; 252/174.21; 252/174.23; 252/DIG. 1; 514/715; 514/717; 514/724; 514/730; 514/941; 514/975; 524/567; 524/569
[58] Field of Search ............ 264/211, 328.17; 252/52 A, 106, 132, 174.21, 174.23, 352, 407, DIG. 1; 424/78, 486; 514/715, 717, 724, 730, 941, 975; 524/366, 367, 369, 370, 376, 379, 381, 383, 384, 385, 391, 567, 569, 755, 761, 762, 765; 2/161 R, 167, 168

[56] References Cited

U.S. PATENT DOCUMENTS

| 1,970,578 | 8/1934 | Schoeller et al. | 558/48 |
| 2,774,709 | 12/1956 | Mayhew et al. | 514/747 |
| 4,040,997 | 8/1977 | Van Vonno et al. | 524/178 |
| 4,393,871 | 7/1983 | Vorhauer et al. | 128/833 |
| 4,544,694 | 10/1985 | Bower | 524/385 |
| 4,581,028 | 4/1986 | Fox, Jr. et al. | 623/2 |

OTHER PUBLICATIONS

Griffin, W. C. "Classification of Surface-Active Agents by HLB". *Journal of the Society of Cosmetic Chemists,* 1949, pp. 311-326.
Feb. 14, 1990, Press Release-Brussels-S. Sprecher-Goldberger.

*Primary Examiner*—Leo B. Tentoni
*Attorney, Agent, or Firm*—Kay H. Pierce; Paul C. Flattery; Susan B. Fentress

[57] ABSTRACT

The present invention relates to infection resistant materials and or products made from a molten blend of at least one polymer and a compound having antioxidant, plasticizer and antiviral activity. Additionally, this compound has a hydrophilic lipophilic balance of between 12 and 20. The preferred polymer, polyvinyl chloride, is blended with the antioxidant, plasticizer, antiviral compound NONOXYNOL-9 (α-nonylphenyl-w-hydroxypoly(oxy-1, 2-ethanediyl) to form the infection resistant material.

5 Claims, 14 Drawing Sheets

INFECTION RESISTANT PRODUCTS

This is a continuation of application Ser. No. 07/484,137, filed on Feb. 22, 1990, now abandoned.

The invention relates therefor also to infection resistant devices obtained by said method or process, to a compound used as antioxidant, plasticizer and as antiviral agent and to a composition of polymer(s) for said method or process.

THE PRIOR ART

It is known that, for manufacturing devices from a molten blend of a polymer, it is suitable to add same additives such as plasticizer(s) and antioxidant(s)

It is also known to cover devices with a layer containing an antibacterial agent. For covering such devices, a composition containing a polymer, a solvent of said polymer and an antibacterial agent is prepared, said composition being then applied on the surface of the device so that, after drying, the device is provided with an antibacterial polymeric layer. Such devices are expensive and have antibacterial properties only on one surface thereof.

It is known to add to molten polyvinyl chloride benzoate of sodium or mercury salts for avoiding a microbial growth on said polymer. However, such additives are toxic for the health so that the use thereof has to be proscribed.

NONOXYNOL-9 (α-(nonylphenyl)-w-hydroxypoly(oxy-1,2,ethanediyl), a non-ionic surfactant of the general formula 1, has been described as an inhibitor of the growth of several microbes such as herpes simplex virus, HTLV-III. NONOXYNOL-9 (α-(nonylphenyl)-w-hydroxypoly(oxy-1,2, ethanediyl)-9 has already been used in spermicides.

Applicant s have found that compounds of the general formule 1

  (1)

are antiviral agents, plasticizers and antioxidants, which are stable at temperature higher than 100° C., so that they may be used in usual injection, extrusion, or other transformation processes.

BRIEF DESCRIPTION OF THE INVENTION

The invention relates to a method for producting infection-resistant materials, devices or part thereof from a molten blend of at least one polymer in which at least a compound of the general formula 1:

$R_1-O-((CH_2)_{a_i}-O)_n-R_2$ where
$R_1$ is a saturated or unsaturated hydrocarbon group;
$a_i$ is, for $i=1$ to n, an integer greater or equal to
$R_2$ is an organic group possibly substituted, and
n is an integer selected so that the Hydrophilic Lipophilic Balance of said compound is comprised between 12 and 20
is mixed with said polymer, said compound acting as an antioxidant, as a plasticizer and as an antiviral agent.

Said molten blend may thus, for example, be:
extruded, injected or dip moulded so as to manufacture infection-resistant materials or devices; or
sprayed on materials or devices so as to provide said materials or devices with a infection-resistant layer.

The invention relates also to infection resistant devices for example surgical gloves, surgical clothes, surgical operative fields, finger stalls, aprons, bibs, caps, etc, manufactures for example by injecting into a mould a molten blend of a polymer mixed with a compound of formula 1 in which $R_1$, $a_i$, n and $R_2$ have the aforementioned meanings.

The invention relates to compounds of general formula 1 and to composition of polymer(s) containing a compound of formula 1, said compounds or/and compositions being suitable for the manufacture of infection-resistant devices according to the invention.

DESCRIPTION OF THE INVENTION

Compounds of general formula 1:

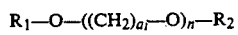

are known as being non-ionic surfactants.

Said compound may be characterized by a hydrophile-lipophile balance (HLB) as teached by GRIFFIN, W.C. (1949), J. Soc. Cosmet. Chem.1, 311–326.

Such compounds are, for example, alkylphenoxypoly (ethyleneoxy) ethanol and more specifically nonylphenoxypoly (ethyleneoxy)ethanol ANTAROX CO-630 (nonylphenoxypoly (ethyleneoxy)ethanol) and NONOXYNOL (α-(nonylphenyl)-w-hydroxypoly(oxy-1,2,ethanediyl).

Methods for the manufacture of such compounds are given for example, in U.S. Pat. No. 1,970,578 and U.S. Pat. No. 2,774,709.

Compounds which are suitable are compounds of the general formula 1:

  (1)

where
$R_1$ is a saturated or unsaturated hydrocarbon group;
$a_i$ is, for $i=1$ to n, an integer greater or equal to 2;
$R_2$ is an organic group possibly substituted, and
n is an integer selected so that the Hydrophilic Lipophilic Balance of said compound is comprised between 12 and 20.

It has been found that said compounds when treated at temperature higher than 100° C. have always virucide action for example against Hepatitis A, Hepatitis B and AIDS (HTL VIII). The compounds were even stable at temperature of about 200° C.

In a method according to the invention, compound of general formula 1 in which $R_1$, $R_2$, $a_i$ and n have the above given meanings is mixed with a plasticizer before being added to a molten polymer. When manufacturing for example disposable gloves, the compound of general formula 1 will be distributed between the surface and the polymer matrix. Therefor, the infection-resistant devices according to the invention provide an antiviral contact protection and a protection mechanism in case of pinholes or microcracks.

Since the compounds of formula 1 in which $R_1$, $R_2$, $a_i$ and n have the above given meanings does not affect the polymer network properties, such as tensile strength, elasticity modules, etc up to 10% or even more of said compounds may be added.

Moreover since said compounds of formula 1 have a similar plastificating effect as known plasticizers such as di iso nonyl phthalate (DINP), dialkylhexylphthalate, etc the compounds of formula 1 may replace the plasticizers.

The used compound of general formula 1 has preferably the following characteristics:

$R_1$ is a possibly substituted cycloalkyl or aromatic radical advantageously a phenyl radical substituted by at least one alkyl group and preferably a phenyl radical substituted in para position with a $C_{6-12}$ alkyl group;

$a_i$ is 2 or 3;

n is an integer comprised between 6 and 20, preferably between 8 and 15, and $R_2$ is a radical selected from the group consisting of hydrogen and/or alcohol.

Polymers which may be used in said method are polyethylene (low density, high density), polypropylene, polyvinylchloride, polystyrene, polyamide, polycarbonate, and rubber.

The $C_{6-12}$ alkyl group which is used as substituent in para position of the phenyl radical may be selected from the group consisting of linear alkyl group such as n-hexyl, n-heptyl, n-octyl, n-nonyl, n-decyl, n-undecyl and n-dodecyl and branched alkyl group such as methyl pentyl, methyl heptyl, methyl octyl, methyl nonyl, methyl decyl, methyl undecyl, di-methyl hexyl, 4-(tert-octyl) and, ethyl propyl.

Preferred alkyl groups are n-octyl, n-nonyl, 4-(tert octyl), 7-methylheptyl, 6-dimethylhexyl, 8-methyloctyl and, 7-dimethylheptyl.

EXAMPLES AND TESTS

Example of Compounds

Compounds which are suitable for the method according to the invention are compounds of formula $$R_1-O-((CH_2)_2-O)_n-H$$

in which $R_1$ is —⟨phenyl⟩—$C_9H_{19}$ and n is an integer comprised between 7-8 and 15.

Such compounds are given hereafter:

| TRADEMARK | n | Hydrophilic Lipophilic Balance | FIGS. |
|---|---|---|---|
| ANTAROX ® CO-610 nonylphenoxypoly-(ethyleneoxy) ethanol (sold by GAF CHEMICAL CORP., U.S.A.) | 7-8 | 12.2 | 1 |
| ANTAROX ® CO-620 nonylphenoxypoly (ethyleneoxy) ethanol | 8-9 | 12.6 | 2 |
| ANTAROX ® CO-630 nonylphenoxypoly (ethyleneoxy) ethanol | 9 | 13.0 | 3 and 4 |
| ANTAROX ® CO-660 nonylphenoxypoly-(ethyleneoxy) ethanol | 10 | 13.2 | 5 |
| ANTAROX ® CO-710 nonylphenoxypoly (ethyleneoxy) ethanol | 10-11 | 13.6 | 6 |
| ANTAROX ® CO-720 nonylphenoxypoly (ethylenoxy) ethanol | 12 | 14-2 | 7 |
| ANTAROX ® CO-730 nonylphenoxypoly (ethyleneoxy) ethanol | 15 | 15 | 8 |

The chromatograms of said compounds are given in FIGS. 1 to 8. In said figures curve A is the chromatogram at 225 nm, curve B is the chromatogram at 254 nm and curve C is the chromatogram at 271 nm.

It appears from these figures that peaks appear for each compound after about 1.3, 1.6, 1.7, 1.9 and 2.1 minutes.

From this chromatograms, it is clear that the products of the ANTAROX nonylphenoxypoly(ethyleneoxy) ethanol family may be considered as a mixture of various compounds, n being only a mean value.

Figure 1:
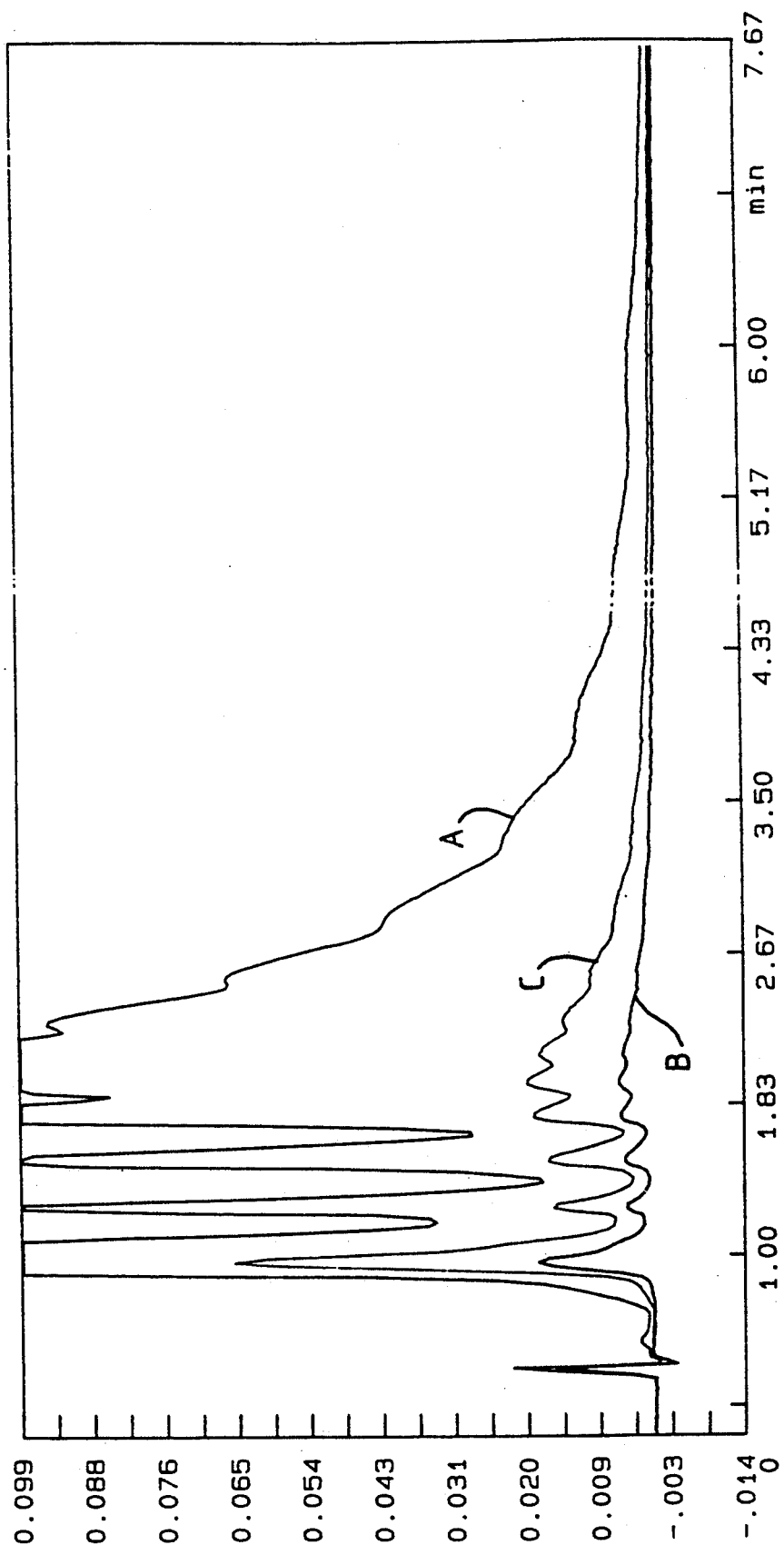
FIGS. 1 to 8 are chromatograms at 225, 254 and 271 nm of compounds suitable for the method according to the invention.
Figure 2:
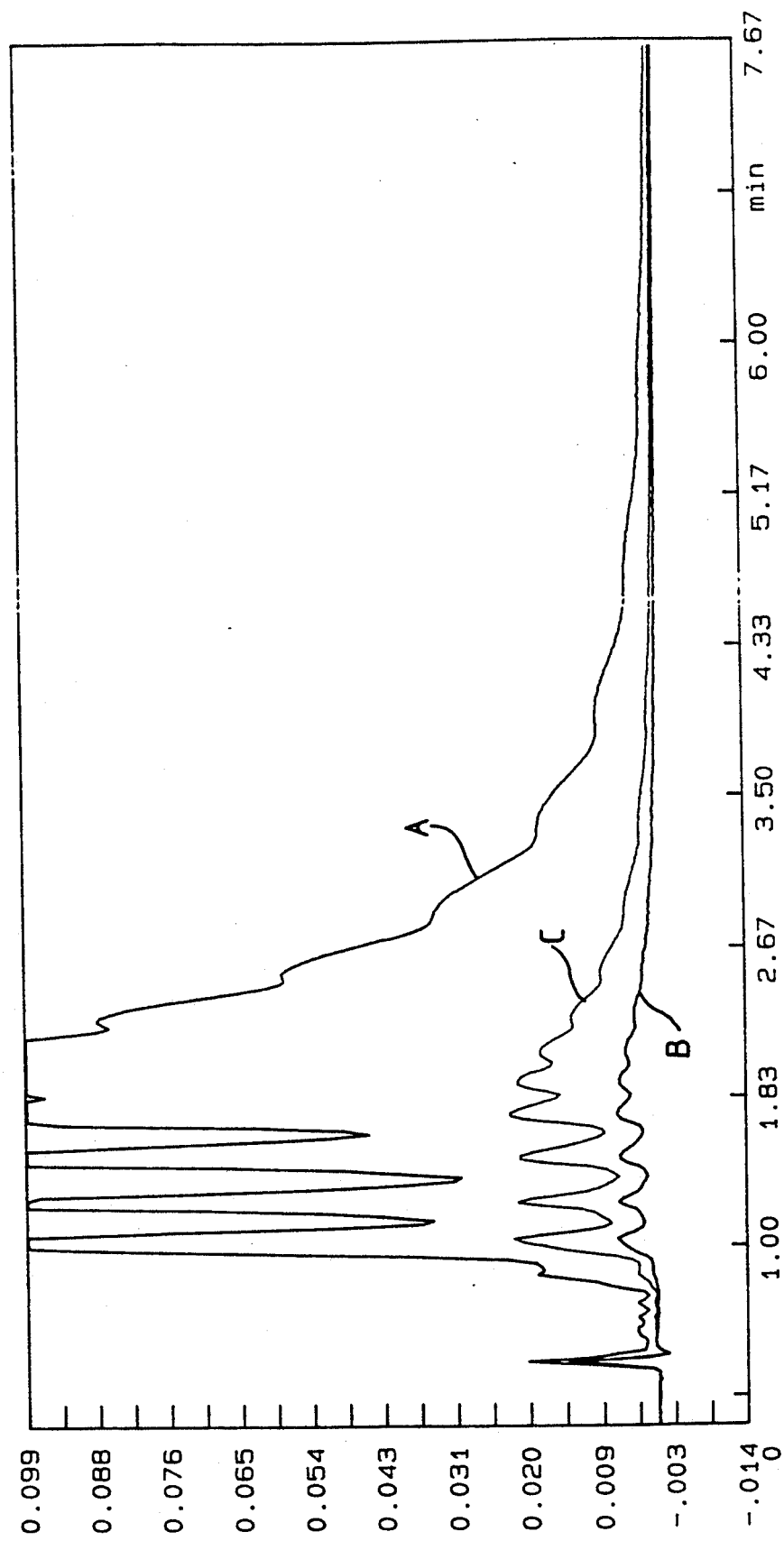
Figure 3:
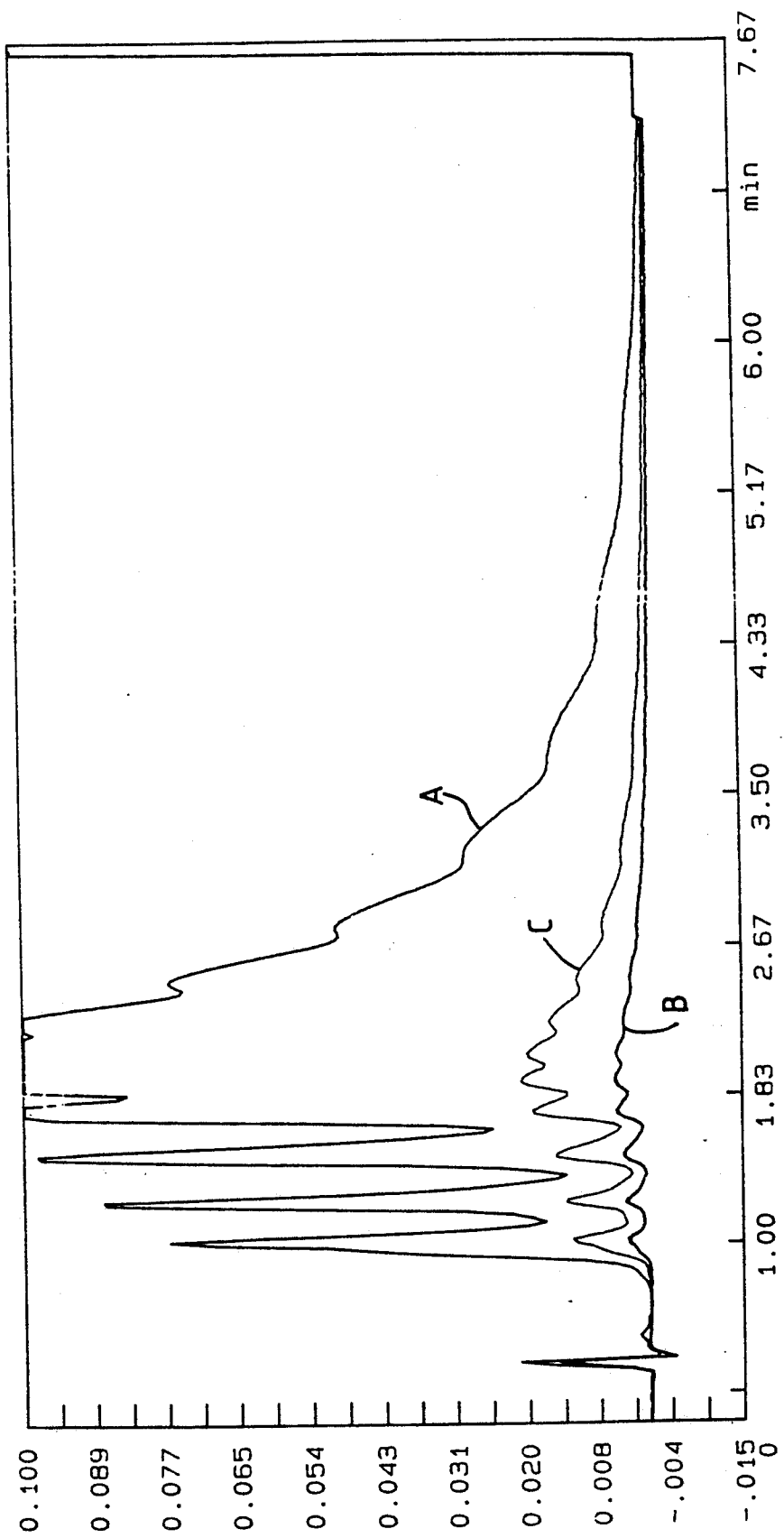
Figure 4:
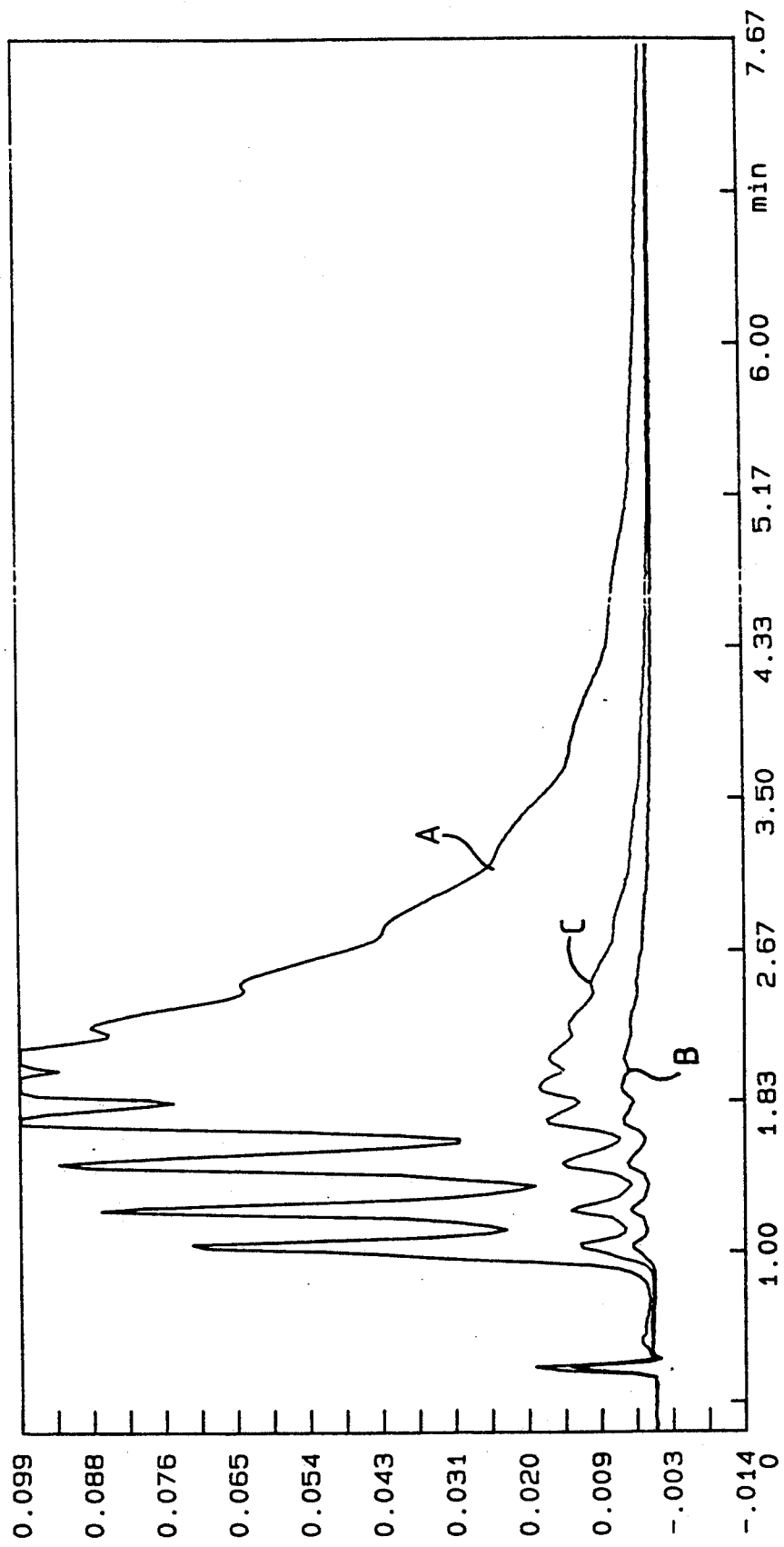
Figure 5:
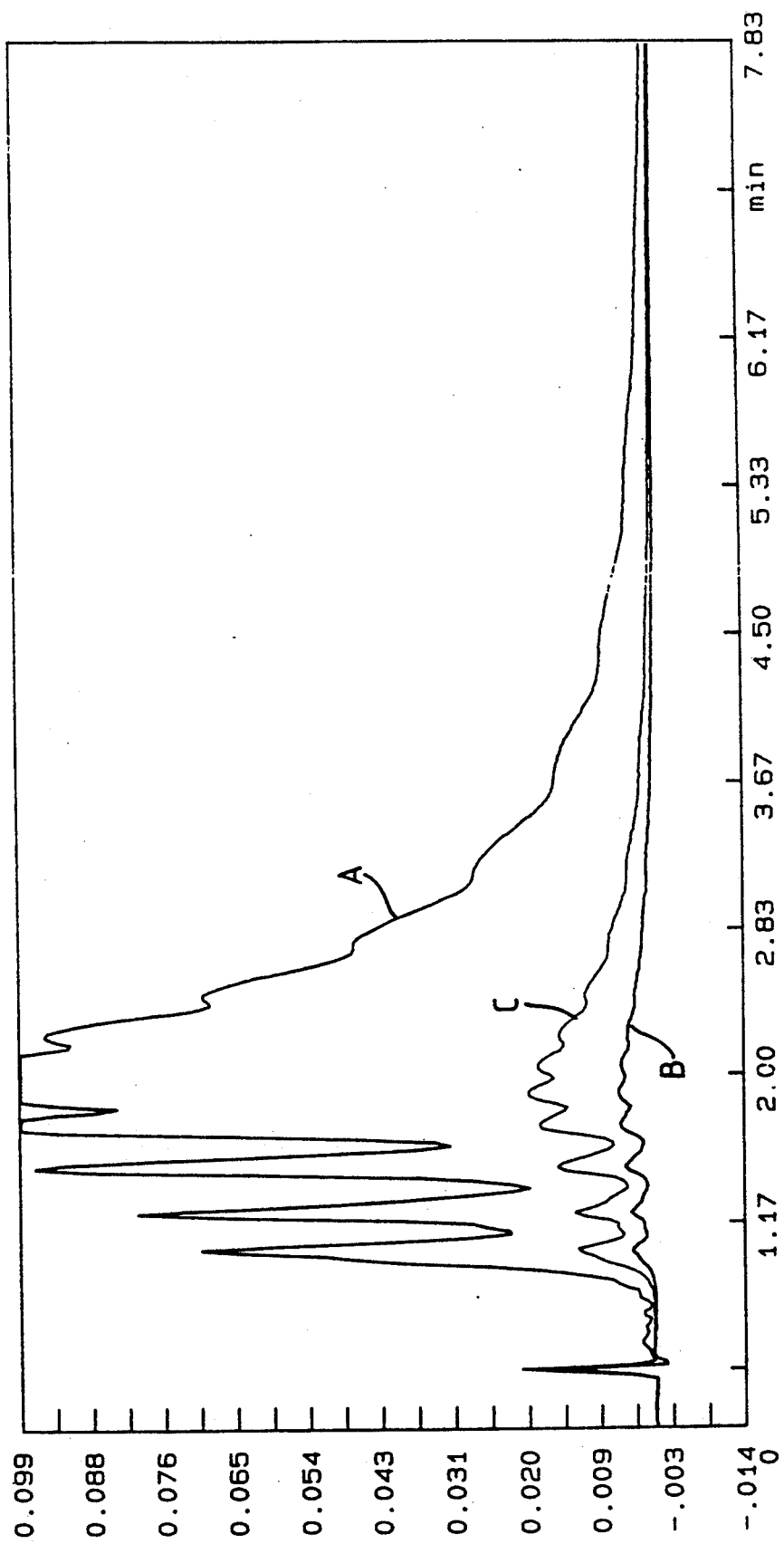
Figure 6:
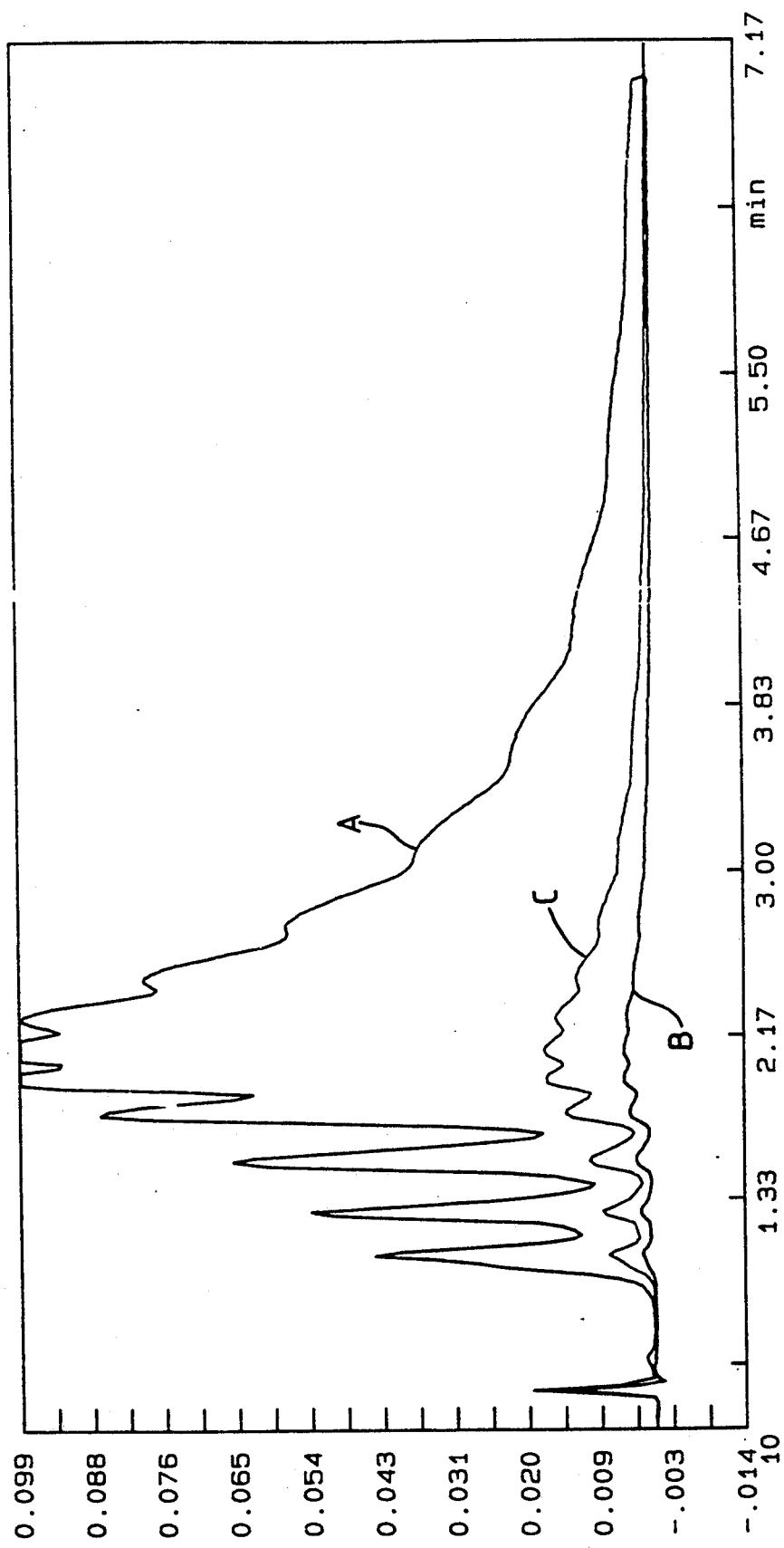
Figure 7:
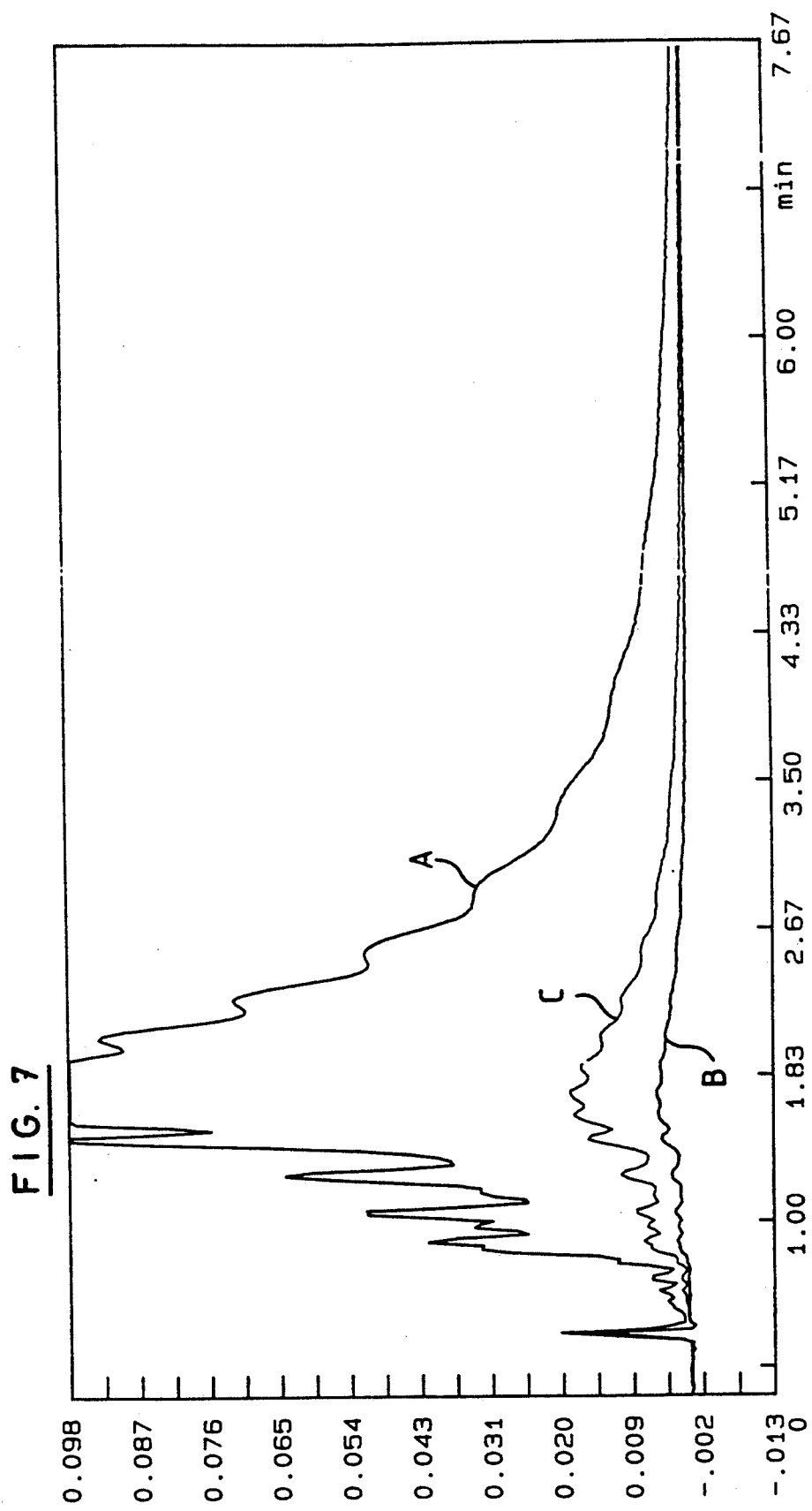
Figure 8:
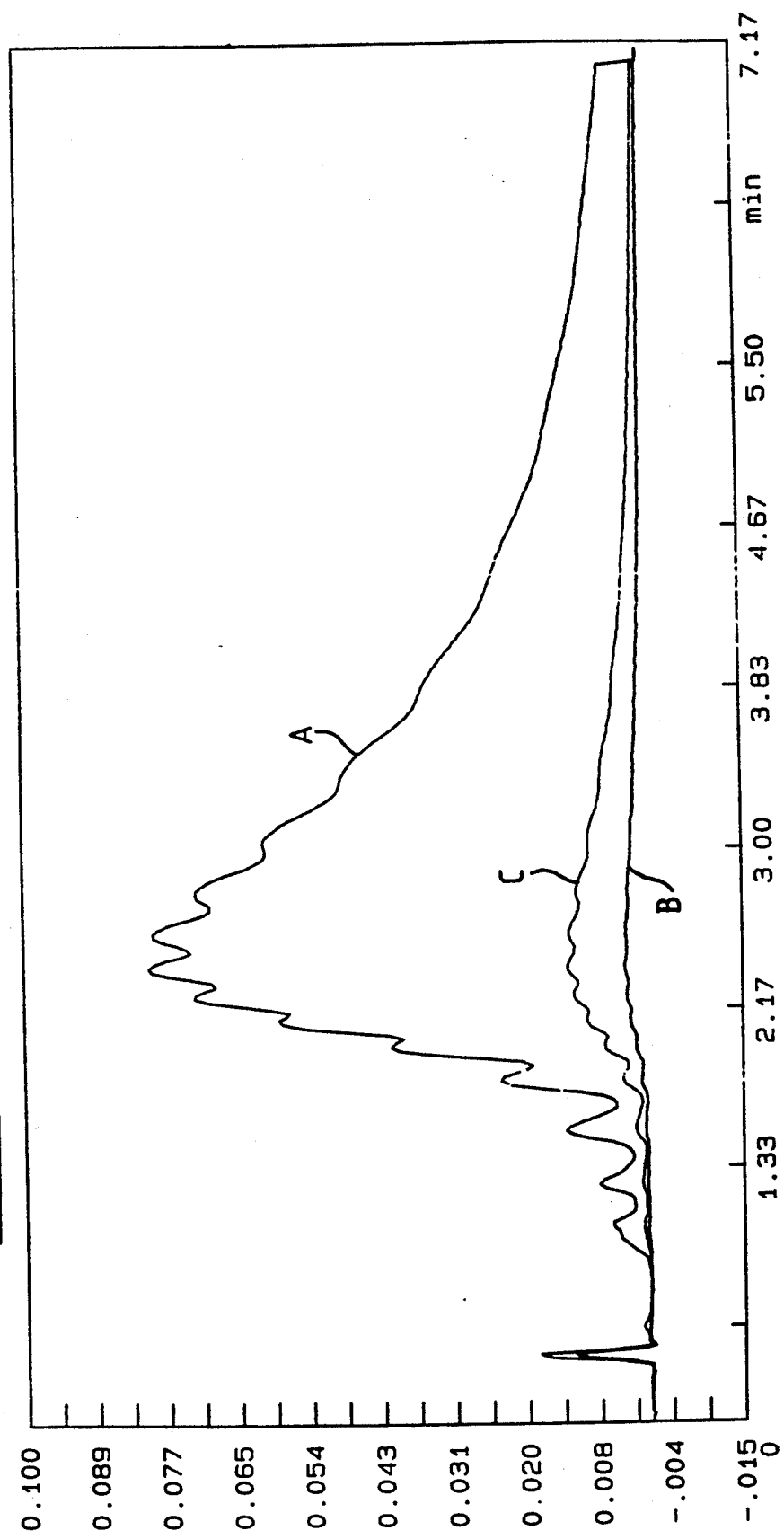
Figure 9:
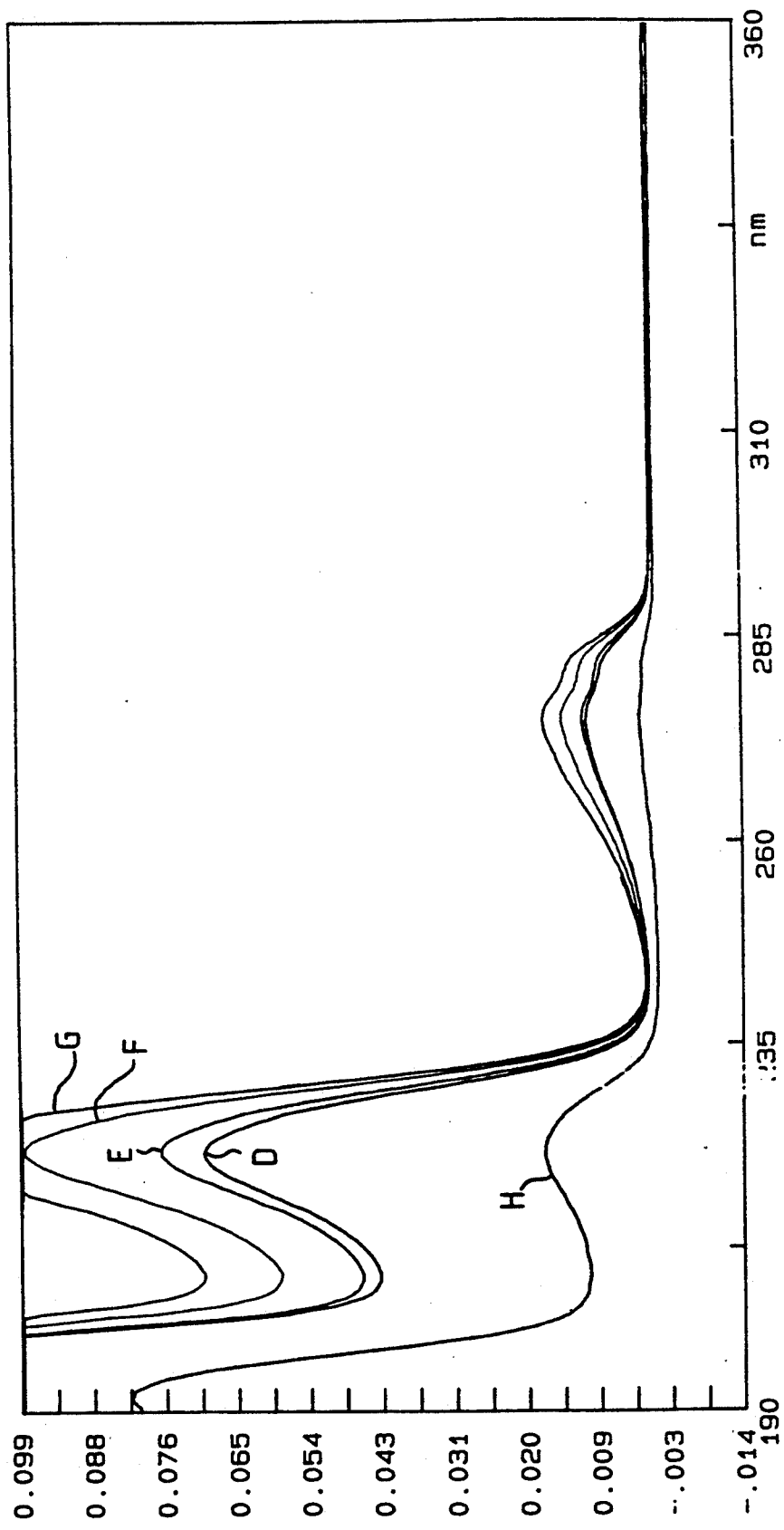
FIG. 9 is a UV spectrum of a compound suitable for the method according to the invention.

ANTAROX ® CO-630 nonylphenoxypoly(ethyleneoxy) ethanol (normal grade) has been analyzed via a UV spectrum (see FIG. 9). In said FIG. 9, curves D, E, F, G and H represent the UV spectrum of the fraction of the compound ANTAROX nonylphenoxypoly(ethyleneoxy) ethanol appearing on the chromatogram at respectively 1.04, 1.26, 1.52, 1.78 and 3.78 minutes.

It appears from this UV analysis that ANTAROX CO-630 nonylphenoxypoly(ethyleneoxy) ethanol contains various compounds having the following structure $H_{19}C_9-C_6H_4-O-(CH_2-CH_2-O)_{n_i}-H$ and that the n value given to ANTAROX CO-630 nonylphenoxypoly(ethyleneoxy) ethanol is a mean value of the various $n_i$.

Another example of non ionic surfactant of the formula 1 which is suitable for the method according to the invention is:

$$H_3C-\underset{\underset{CH_3}{|}}{\overset{\overset{CH_3}{|}}{C}}-CH_2-\underset{\underset{CH_3}{|}}{\overset{\overset{CH_3}{|}}{C}}-\text{⟨phenyl⟩}-O(CH_2-CH_2-O)_{\overline{n}}H$$

n being equal to 9-10.

Said compound is sold by BOEHRINGER MANNHEIM LABORATORIES under the name TRITON ® X-100 nonylphenoxypoly(ethyleneoxy) ethanol.

It is clear that mixture of compounds of general formula 1 may be used as antivirus agent, plasticizer and antioxidant.

Thermal Stability Tests

The stability of blends containing compounds ANTAROX ® CO-630 nonylphenoxypoly(ethylereoxy) ethanol (normal grade) has been shown by means of the following test.

A sample of polyvinyl chloride has been heated on the following manner:

0 to 3 minutes the sample is heated at 55° C. under nitrogen, from 3 minutes to 6 minutes the temperature of the sample under nitrogen is increased at a rate of 40° C. per minutes, from 6 minutes to 46 minutes (end of the test) the temperature of the sample is maintained at 175° C. and a flow of oxygen is applied on the sample, the thermal response of which is studied by means of a Perkin Elmer Thermal Analysis System.

Figure 10:
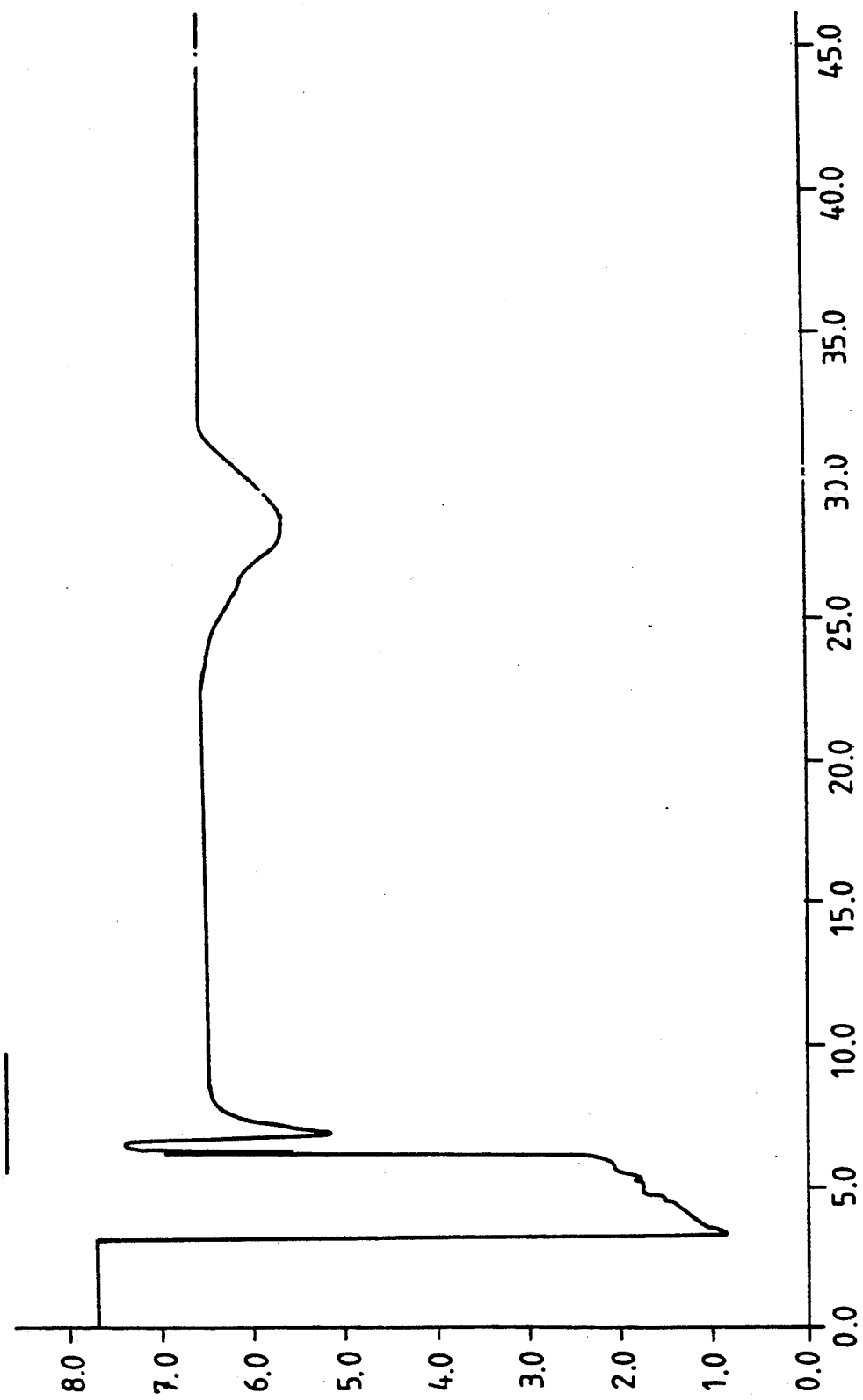
FIGS. 10 to 12 show the stability of polyvinylchloride at 175° C.
Figure 11:
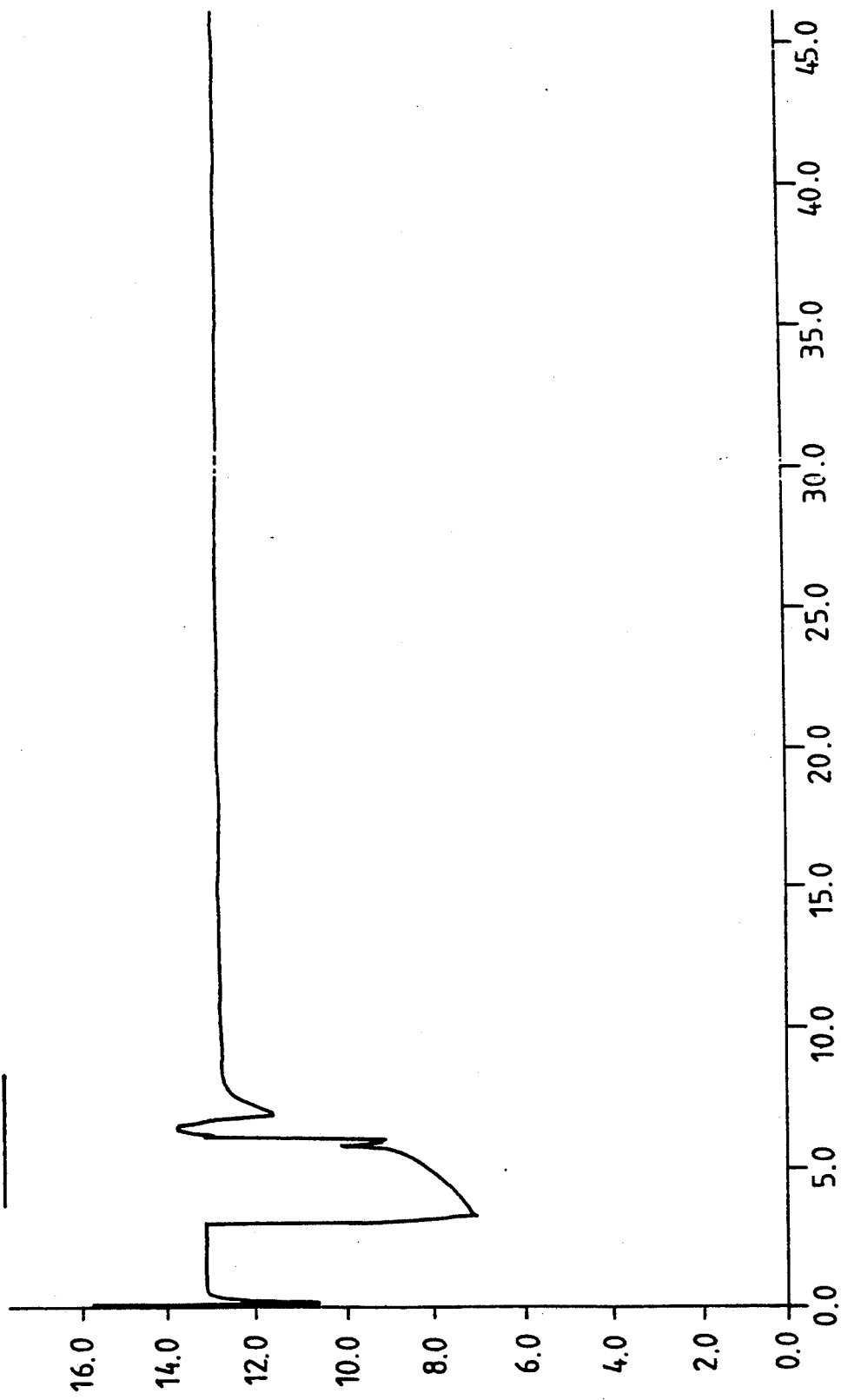
Figure 12:
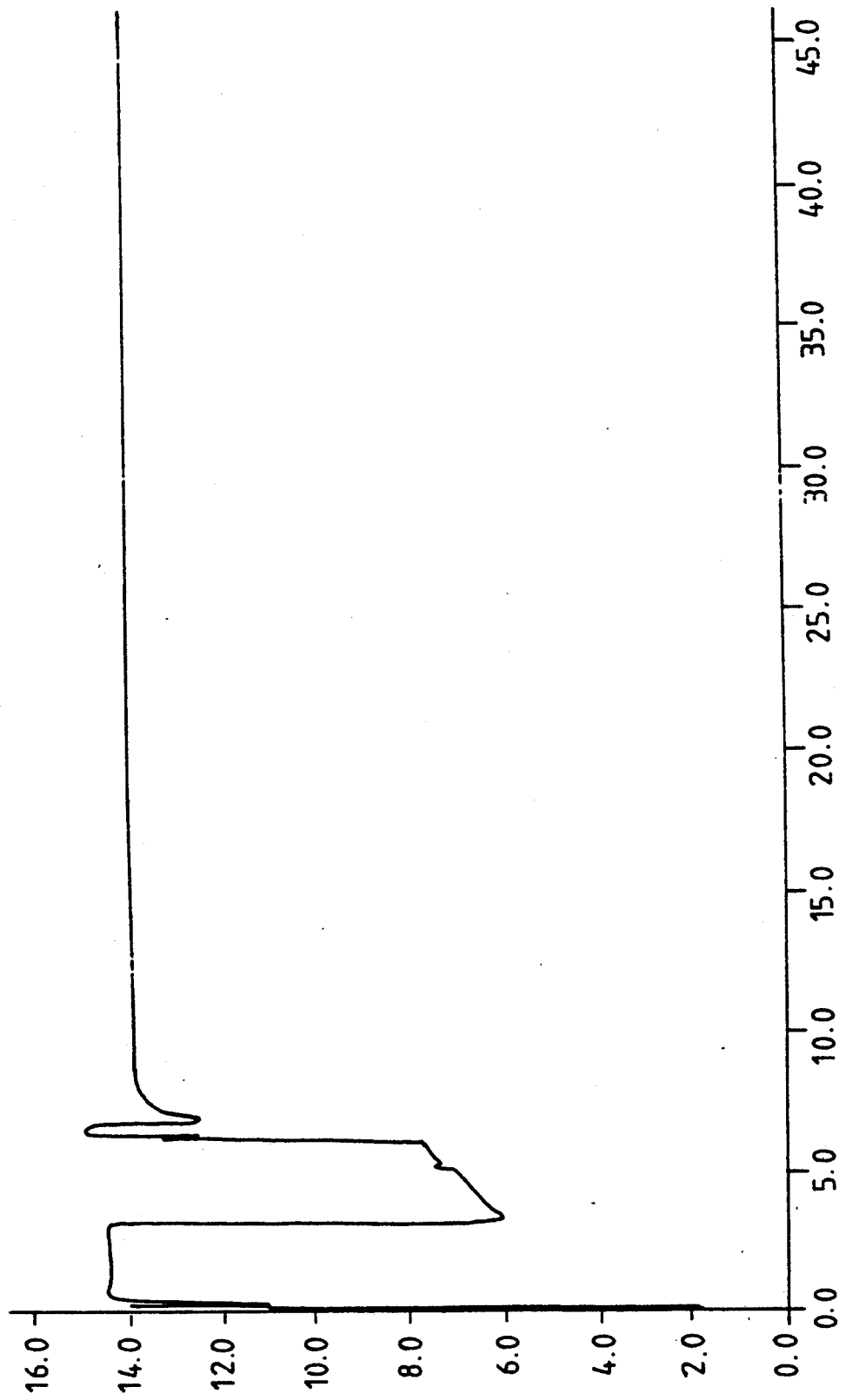

FIGS. 10 to 12 show the thermal response of polyvinylchloride sample i.e. the heat flow (mW) required for heating the sample (P) or for the melting thereof (Q) or for maintaining a temperature of 175° C. (R) after a time of X minutes.

If a variation of heat flow occurs while maintaining a temperature of 175° C., it means that the sample is oxidized or degraded.

FIG. 10 shows the termal response of a polyvinylchloride sample, with the standard plasticizer (DINP) while FIG. 11 and FIG. 12 show the influence of replacing the standard plasticizer with an equivalent amount of Antarox CO-630 polyoxyethylated nonylpenol, respectively for 5 and 10% of the formulation concentration.

It appears from these figures that the addition of ANTAROX CO-630 nonylphenoxy-poly(ethyleneoxy) ethanol increases the stability of the PVC sample. It means also that ANTAROX CO-630 nonylphenoxypoly(ethylencoxy) ethanol is stable at temperature of 175° C. so that said compound may be used in usual techniques such as polymer injection, extrusion, . . . without any degradation.

Examples of manufacture 95 kg of liquid plastisol, (a blend containing 45% of polyvinyl chloride, the rest essentially DINP) is mixed with 5 kg of ANTAROX ® CO-630 nonylphenoxypoly(ethyleneoxy) ethanol. Said composition has been cast so as to produce film samples for mechanical tests, after gelification at 175° C.

During the mixing of ANTAROX ® CO-630 nonyl phenoxy poly(ethyleneoxy) ethanol, with the plastisol, no phase separation was observed.

The tensile strength of samples was estimated by tests performed with a rate of 200 mm/min.

A surface migration of ANTAROX nonyl phenoxypoly(ethyleneoxy) ethanol was observed for the films, the thickness of which was approximative 130 microns.

In a same manner, films samples were manufactured from a composition containing 90 kg of plastisol and 10 kg of ANTAROX ® CO-630 nonylphenoxypoly(ethyleneoxy) ethanol.

A surface migration was also observed for the gloves, the thickness of which was about 130 microns.

The mechanical properties of the casted film samples are summarized in the following table. For comparison purpose said table contains also mechanical properties of samples made only from plastisol.

TABLE

|  | plastisol | plastisol +5% ANTAROX | Plastisol +10% ANTAROX |
| --- | --- | --- | --- |
| Tensile Strength N/mm$^2$ | 8.1 | 6.94 | 5.9 |
| Elongation % | 217 | 241 | 243 |

When using gloves containing ANTAROX ® CO-630, nonylphenoxypoly-(ethyleneoxy) ethanol, no allergic reaction of the users was observed.

Further advantage

The gas permeability of polyvinylchloride with or without Antarox CO-630 nonylphenoxypoly(ethyleneoxy) ethanol has also been studied.

For this study, samples are set in a measuring chamber comprising two parts, the lower of which being the circulation and sampling system while the upper part is the gassing chamber.

The working gas was constituted of respectively one third of carbon dioxide ($CO_2$), one third of oxygen ($O_2$) and one third of nitrogen ($N_2$), said gas flowing in the upper part.

Said gas passes through the PVC film and is periodically swept by helium gas (vector gas) to the detector where it is quantified.

Figure 13:
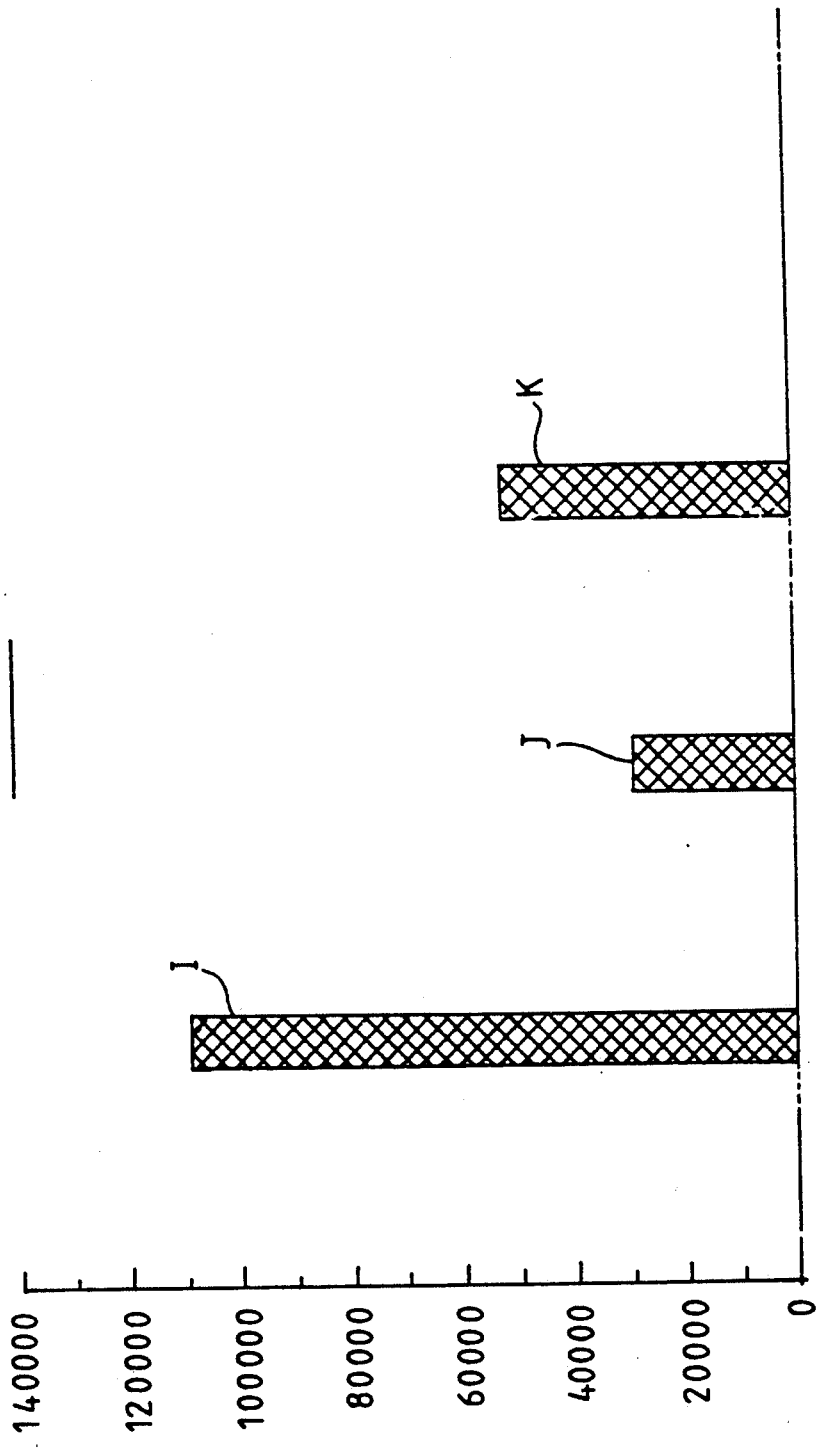
FIGS. 13 and 14 show permeabilities of polyvinylchloride.
Figure 14:
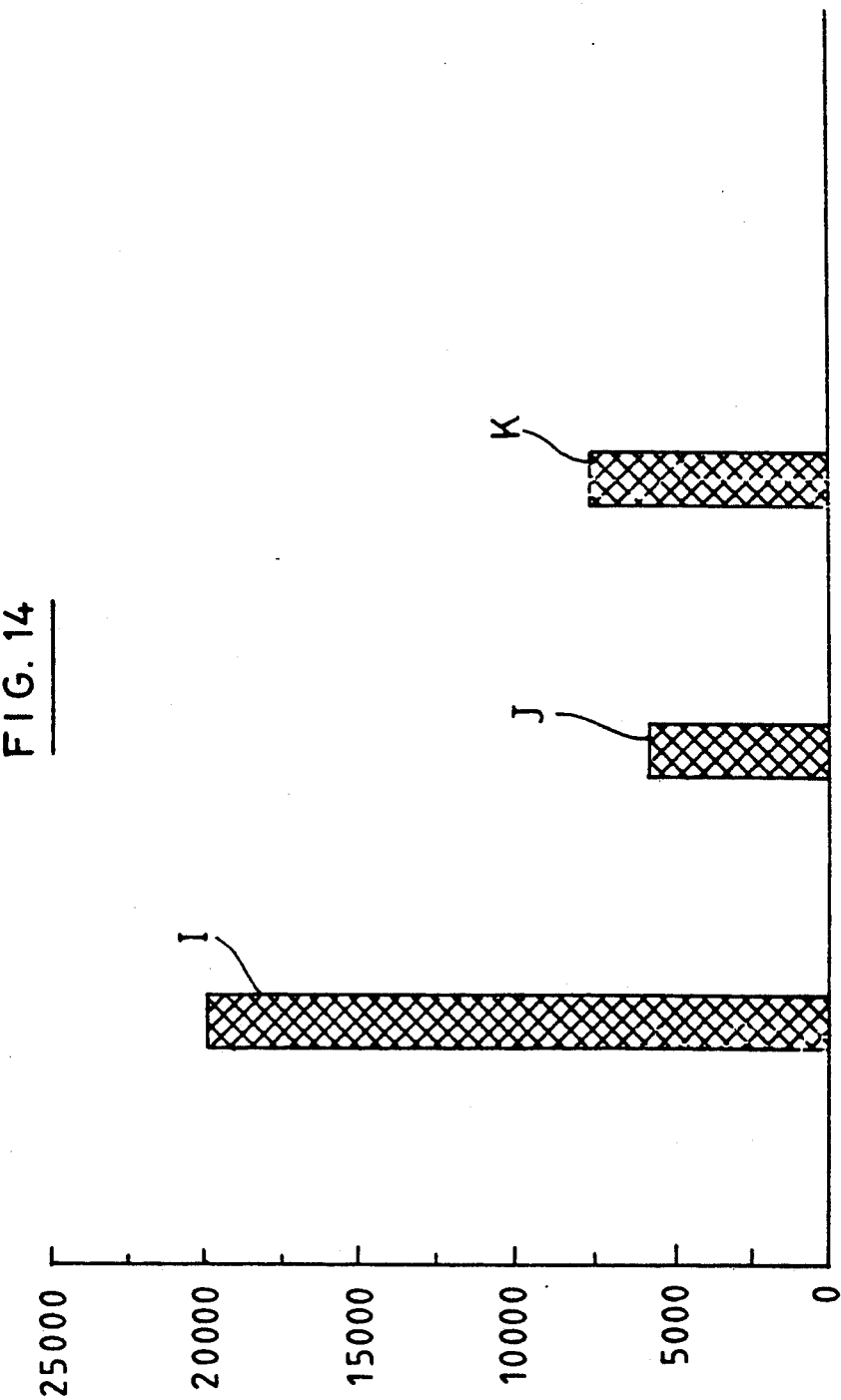

The permeabilities of the films without ANTAROX nonylphenoxypoly(ethyleneoxy) ethanol (film I, plastisol), of the film containing 5% ANTAROX CO-630 nonylphenoxypoly(ethyleneoxy) ethanol (film J) and of the film containing 10% Antarox CO-630 nonylphenoxypoly(ethyleneoxy) ethanol (film K) are given in FIG. 13 for $CO_2$ and in FIG. 14 for $O_2$, said permeabilities being expressed in cm$^3$/day m$^2$ atm.

Devices and materials obtained by the process according to the invention are thus effective for making gas barrier.

The replacement of known plasticizer such as DINP BY ANTAROX CO-630 nonylphenoxypoly(ethyleneoxy) ethanol allow to reduce the gas permeability. Therefor it seems that devices and materials obtained by the process according to the invention have pinholes, the dimensions of which or the number of which are lower than devices and materials which do not contain a compound of formula 1 in the matrix of the polymer. In other words, materials and devices according to the invention have a low porosity.

The gas barrier property of films or materials obtained by the process according to the invention are improved when the composition contains at least 1% of compound(s) of formula 1, preferably between 2 and 10% and more preferably about 5%.

The viscosity of plastisol is about 800 to 1300 cps at temperature comprised between 30° and 35° C. while the viscosity of plastisol containing 10% ANTAROX ® CO-630 nonylphenoxypoly-(ethyleneoxy) ethanol is about 920 cps at 32° C. Therefor, the use of compounds of formula 1, in particular of Antarox ® CO-630 nonylphenoxypoly(ethyleneoxy) ethanol instead of known plasticizers such as DINP does not require modification of the manufacture process.

What we claim is:

1. Polymeric infection resistant glove comprising a blend of a polymer and a heat resistant antiviral compound made by the process comprising:

a. mixing a molten blend of a polymer and a compound having a Hydrophilic Lipophilic Balance of between 12 and 20, said compound consisting of: $R_1$—O—$((CH_2)a_i$—O$)n$—$R_2$ where $R_1$ is a saturated or unsaturated hydrocarbon radical, the constituent elements selected from the group consisting of carbon, hydrogen and oxygen; $a_i$ is, for i=to n, an integer greater than or equal to 2; $R_2$ is an organic radical, the constituent elements selected from the group consisting of carbon, hydrogen and oxygen n is an integer selected so that the Hydrophilic Lipophilic Balance of said compound is between 12 and 20, said compound comprising between 1 to 10% of said glove; and b. forming said glove.

2. The polymeric infection resistant glove of claim 1 wherein:
   $R_1$ is a radical selected from the group consisting of substituted cycloalkl and substituted aromatic radical;
   $a_i$ is, 2 or 3;
   n is an integer between 6 and 20; and
   $R_2$ is selected from the group consisting of hydrogen and alcohol.

3. The polymeric infection resistant glove of claim 1 wherein said polymer is polyvinyl chloride.

4. The polymeric infection resistant glove of claim 1 wherein said compound is (a-(nonylphenyl-w-hydroxpoly(oxy-1,2, ethanediyl).

5. The polymeric infection resistant glove of claim 1 wherein said compound is (nonylphenoxypoly(ethyleneoxy) ethanol).

* * * * *